United States Patent [19]
Cottrell et al.

[11] Patent Number: 5,801,116
[45] Date of Patent: Sep. 1, 1998

[54] PROCESS FOR PRODUCING POLYSACCHARIDES AND THEIR USE AS ABSORBENT MATERIALS

[75] Inventors: Ian William Cottrell, Yardley, Pa.; Animesh Goswami, Plainsboro; Manjit Singh Chowdhary, Princeton Junction, both of N.J.

[73] Assignee: Rhodia Inc., Cranbury, N.J.

[21] Appl. No.: 880,113

[22] Filed: Jun. 20, 1997

Related U.S. Application Data

[63] Continuation of Ser. No. 418,334, Apr. 7, 1995, abandoned.

[51] Int. Cl.$^6$ .............. B01J 20/00; B01J 20/22; B01J 20/26; A61F 13/15
[52] U.S. Cl. .............. 502/404; 502/401; 502/402; 502/403; 604/368
[58] Field of Search ................ 502/401, 402, 502/403, 404; 604/368

[56] References Cited

U.S. PATENT DOCUMENTS

| | | | |
|---|---|---|---|
| Re. 32,957 | 6/1989 | Elias | 604/368 |
| 2,298,424 | 10/1942 | Schreiber | 604/368 |
| 2,639,239 | 5/1953 | Elliott | 106/197 |
| 2,891,050 | 6/1959 | Elverum et al. | 260/209 |
| 3,005,456 | 10/1961 | Graham | 128/285 |
| 3,528,421 | 9/1970 | Valliancourt et al. | 128/284 |
| 3,563,243 | 2/1971 | Lindquist | 128/287 |
| 3,669,103 | 6/1972 | Harper et al. | 128/156 |
| 3,670,731 | 6/1972 | Harmon | 128/284 |
| 3,683,917 | 8/1972 | Comerford | 604/368 |
| 3,686,024 | 8/1972 | Nankee et al. | 117/140 |
| 3,723,413 | 3/1973 | Chatterjee et al. | 260/232 |
| 3,731,686 | 5/1973 | Chatterjee | 128/285 |
| 3,783,872 | 1/1974 | King | 128/290 |
| 3,898,143 | 8/1975 | Assarsson et al. | 204/159 |
| 3,903,889 | 9/1975 | Torr | 128/287 |
| 3,935,099 | 1/1976 | Weaver et al. | 604/368 |
| 3,936,441 | 2/1976 | Holst et al. | |
| 4,043,952 | 8/1977 | Ganslaw et al. | 260/17.4 |
| 4,055,184 | 10/1977 | Karami | 128/287 |
| 4,066,828 | 1/1978 | Holst et al. | 536/87 |
| 4,068,068 | 1/1978 | Holst et al. | 536/88 |
| 4,069,177 | 1/1978 | Smith | 260/17.4 |
| 4,075,279 | 2/1978 | Holst et al. | 536/88 |
| 4,076,663 | 2/1978 | Masuda et al. | 260/17.4 |
| 4,084,591 | 4/1978 | Takebe et al. | 128/285 |
| 4,200,558 | 4/1980 | Holst et al. | 260/17 |
| 4,200,736 | 4/1980 | Shinohara et al. | 536/87 |
| 4,200,737 | 4/1980 | Marder et al. | 536/87 |
| 4,333,461 | 6/1982 | Muller | 604/369 |
| 4,454,055 | 6/1984 | Richman et al. | 252/194 |
| 4,605,736 | 8/1986 | Morgan | 536/114 |
| 4,624,868 | 11/1986 | Muller | 427/384 |
| 4,650,716 | 3/1987 | Gelman | 428/402 |
| 4,677,201 | 6/1987 | Morgan | 536/114 |
| 4,689,408 | 8/1987 | Gelman et al. | 536/98 |
| 4,727,824 | 3/1988 | Ducharme et al. | 119/1 |
| 4,732,930 | 3/1988 | Tanaka et al. | 524/742 |
| 4,883,021 | 11/1989 | Ducharme et al. | 119/1 |
| 4,952,550 | 8/1990 | Wallach et al. | 502/404 |
| 4,959,464 | 9/1990 | Yeh | 536/114 |
| 5,100,933 | 3/1992 | Tanaka et al. | 523/300 |
| 5,145,906 | 9/1992 | Chambers et al. | 524/732 |
| 5,242,491 | 9/1993 | Mamada et al. | 106/241 |
| 5,274,018 | 12/1993 | Tanaka et al. | 524/166 |
| 5,532,350 | 7/1996 | Cottrell et al. | 536/76 |
| 5,597,873 | 1/1997 | Chambers et al. | 525/330.1 |

FOREIGN PATENT DOCUMENTS

| | | | |
|---|---|---|---|
| 0953889 | 9/1974 | Canada. | |
| 0019371 | 4/1980 | European Pat. Off. | A61L 15/00 |
| 0260135 | 9/1987 | European Pat. Off. | C09K 3/32 |
| 0476574 | 9/1991 | European Pat. Off. | B01J 20/26 |
| 0481225 | 4/1992 | European Pat. Off. | B01J 20/26 |
| 0556118 | 4/1992 | European Pat. Off. | C08B 37/00 |
| 0538904 | 10/1992 | European Pat. Off. | C08B 37/00 |
| 4206850 | 9/1993 | Germany | C08L 1/08 |
| 4206856 | 9/1993 | Germany | C08L 1/00 |
| 4206857 | 9/1993 | Germany | C08L 1/00 |
| 1331964 | 10/1970 | United Kingdom | D04H 1/60 |

OTHER PUBLICATIONS

Superabsorbent Patents Much More Than Just Diapers, by Bernard J. Obenski, Nonwoven Industry, Nov. 1987 pp. 24–26.

High Gel Strength Cellulostic Absorbent Polymers for Absorbing Meat Fluids in Packaging Applications, Res. Disclosure–1993 May 1993–349—pp. 296+ May 1993.

Chemical Abstract–(A 118C12): 109801K, 1992 Month n/a.

Chemical Abstract–(A 116C2): 11260Z, 1991 Month n/a.

*Primary Examiner*—Mark L. Bell
*Assistant Examiner*—Patricia L. Hailey
*Attorney, Agent, or Firm*—Andrew M. Solomon

[57] ABSTRACT

A solid composition of matter comprising one or more polysaccharides which has a coarse particle size is provided. The composition demonstrates absorbent properties and is useful in absorbent articles of manufacture. Also provided is a method for preparing the compositions.

28 Claims, No Drawings

PROCESS FOR PRODUCING POLYSACCHARIDES AND THEIR USE AS ABSORBENT MATERIALS

This application is a continuation, of application Ser. No. 08/418,334 filed Apr. 7, 1995, now abandoned.

BACKGROUND OF THE INVENTION

1. Field of the Invention

This invention relates to novel absorbent materials, a process for preparing these materials and absorbent articles containing the absorbent. More specifically, the absorbent materials comprise polysaccharides which have been synthesized to have a particle size of greater than 200 mesh as measured using a Tyler screen and have a desirable combination of absorbency and gel strength properties.

2. Technology Description

Many attempts have been described in the patent literature to prepare absorbent materials, i.e. materials which are capable of absorbing many times their weight of water or various body fluids.

The following list is representative of United States patents which have issued in this area: U.S. Pat. No. 3,528,421 (disposable absorbent underpad for hospital patients or similar product, hydrous calcium silicate chemical absorbent); U.S. Pat. No. 3,563,243 (absorbent pads such as diapers, underpads and the like-hydrophilic polymer absorbent); U.S. Pat. No. 3,669,103 (absorbent products containing a hydrocolloidal polymeric absorbent lightly cross-linked polymer such as poly-N-vinyl-pyrrolidone, polyvinyltoluenesulfonate, poly-sulfoethyl acrylate, and others); U.S. Pat. No. 3,686,024 (water absorbent articles coated with a water-swollen gel such as cross-linked partially hydrolyzed polyacrylamide); U.S. Pat. No. 3,670,731 (absorbent dressing using water soluble hydrocolloidal composition); U.S. Pat. No. 3,783,872 (absorbent articles such as diapers, and the like using insoluble hydrogels as the absorbing media); U.S. Pat. No. 3,898,143 (disposable absorbent articles using poly(ethylene oxide) and at least one other water soluble polymer co-crosslinked by high energy irradiation); U.S. Pat. No. 4,055,184 (absorbent pads for disposable diapers, sanitary napkins, bandages or the like using solid, finely-divided mixture of a hydrolyzed starch polyacrylonitrile graft copolymer in acidic form and a non-irritating and non-toxic water-soluble basic material); U.S. Pat. No. 4,069,177 (water absorbing and urine stable step-wise grafted starch-polyacrylonitrile copolymers); U.S. Pat. No. 4,076,663 (water absorbing starch resins); U.S. Pat. No. 4,084,591 (absorber for blood made from filaments of a lower alkyl or a lower hydroxyalkyl substituted cellulose ether).

In U.S. Pat. No. 3,903,889 the patentee describes as an absorbent composition for use in absorbent products a guar gum which is modified with borate anion in an amount sufficient to complex the gel formed from the hydration of guar gum alone. Specifically, the patentee teaches introducing borate ion into the absorbent product in the form of an essentially water insoluble borate-release agent in which the free borate ion is released slowly to the absorbent system and only after the aqueous liquid sought to be absorbed by the product has entered the product itself. It is suggested that the modified guar gum can absorb up to at least 20 times its weight of water to produce a relatively dry non-sticky and inert gel.

U.S. Pat. Nos. 4,333,461 and 4,624,868 are directed to absorbent materials which comprise borate cross-linked polysaccharides. The enabled polysaccharides are guar gum and its derivatives.

U.S. Pat. No. 4,952,550 is directed to particulate absorbent materials which are carboxylated cellulosic materials. More specifically, the materials are cellulosic base materials which are reacted with a cross-linking agent and a hydrophobicity agent. Preferred cross-linking agents include metals such as aluminum, iron or chromium. Similarly, Research Disclosure 349,296 suggests the use of aluminum cross-linked cellulose gums as absorbent materials.

Other patent documents discuss the use of finely divided polygalactomannan powder materials in absorbent articles of manufacture. They include EP 0 260 135; U.S. Pat. No. 3,070,095; U.S. Pat. No. 3,347,236; U.S. Pat. No. 3,645,836; and U.K. Patent No. 1,331,964. A primary limitation in the use of such materials, which have a particle size of less than 200 mesh as measured by using a Tyler screen (i.e., mesh number is 200 or greater) is that they do not possess the requisite gel strength necessary for certain absorbent applications and that they migrate during manufacture, shipment storage or use, limiting their utility. To overcome the migration problem, U.K. Patent No. 1,331,964 suggests adhering the powder to other fibrous materials. U.S. Pat. No. 3,347,236 suggests forming fibrous materials by adding guar flour to an organic liquid to form a slurry, adding water to the slurry to precipitate a hydrate of the guar, and extruding the resulting hydrate. U.S. Pat. No. 3,645,836 suggests adding water to guar gum to form a hydrate, adding an organic liquid to form a fibrous precipitate and drying the fibrous material.

Other known absorbent materials include those derived from acrylic polymers and those derived from amino acids.

Except for the polyacrylates and starch grafted acrylates, with respect to their application for absorbing or holding fluids such as in diapers, sanitary napkins, bandages, gloves, sporting goods, pet litter and the like the absorbent materials and absorbent products described in these references have not been commercially acceptable. Such problems as insufficient absorbing capacity, insufficient rigidity of the swollen gel, breakdown of the gel structure upon contact with saline fluids, incompatibility with absorbent articles, still exist.

U.S. Pat. Nos. 4,605,736 and 4,677,201 are directed to cross-linking polygalactomannans with a titanium based cross-linking agent. The in situ cross-linking reaction is performed in an aqueous environment and the polygalactomannan is not recovered. These aqueous systems are suggested for use in oil recovery.

U.S. Pat. No. 4,959,464 is directed to the production of aluminum cross-linked derivatized polygalactomannans. The resulting products are suggested for use as thickening agents which readily hydrate under alkaline pH conditions.

Despite the above teachings, there still exists a need in the art for novel compositions which have functionality as absorbent materials.

BRIEF SUMMARY OF THE INVENTION

In accordance with the present invention novel solid compositions are provided which have functionality as absorbent materials. More specifically, the solid compositions comprise one or more polysaccharides having a mean particle size of greater than about 200 mesh, a gel strength of greater than about 2000 dynes per square centimeter and an absorbency of greater than about 15 grams of saline solution per gram of polysaccharide when immersed in a 0.9% saline solution for a time period of one hour.

Particularly preferred polysaccharides include cellulose materials, and polygalactomannans such as guar gum and locust bean gum. Particularly preferred are the use of guar polymers. The polysaccharide materials may be used alone as absorbent materials or may be combined with other known materials such as carbohydrates, natural or synthetic hydrophilic polymers, hydroxylated compounds, carboxylic acids, hydroxyacids, amino acids, peptides and proteins. The absorbent materials may also be combined with conventional materials commonly used for their absorbent properties.

An additional embodiment of the present invention comprises an absorbent article of manufacture including an absorbent solid composition comprising one or more polysaccharides having a mean particle size of greater than about 200 mesh, a gel strength of greater than about 2000 dynes per square centimeter and an absorbency of greater than about 15 grams of saline solution per gram of polysaccharide.

Particularly preferred article of manufactures include diapers, diaper pads, feminine hygiene articles, wound dressings, pet litter, cosmetics, personal care products, pharmaceuticals, textiles, agricultural chemicals, paper materials, construction materials, energy materials, communications materials, food packaging products and the like.

Still another embodiment of the present invention comprises a process for producing a polysaccharide having utility as an absorbent. The process comprises (a) hydrating guar gum splits to a hydration level of between about 20 and about 100

(b) grinding the hydrated guar gum splits to a mean particle size of greater than about 200 mesh; and (C) drying said splits.

In a particularly preferred embodiment, the splits may be extruded after hydration.

An object of the present invention is to provide novel absorbent compositions.

Still another object of present invention is to provide novel absorbent articles of manufacture.

A further object of the present invention is to provide a process for producing compositions which have excellent utility as absorbent materials.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention provides absorbent solid compositions comprising one or more polysaccharides having a mean particle size of greater than about 200 mesh, a gel strength of greater than about 2000 dynes per square centimeter and an absorbency of greater than about 15 grams of saline solution per gram of polysaccharide when immersed in a 0.9 percent saline solution for one hour. The polysaccharides are either water insoluble or slightly soluble (less than 50 percent, preferably less than 30 percent, and even more preferably less than 20 percent of the polysaccharide dissolves in water).

The compositions are polysaccharides, preferably polygalactomannans. The polygalactomannans may be derivatized, having a degree of substitution and/or a molar substitution of between about 0 and about 3.0.

The polygalactomannans are naturally occurring polysaccharides composed principally of galactose and mannose units and are usually found in the endosperm of leguminous seeds, such as guar, locust bean, honey locust, flame tree, and the like. Guar flour, for example, is composed mostly of a galactomannan which is essentially a straight chain mannan with single membered galactose branches. The mannose units are linked in a 1-4-β-glycosidic linkage and the galactose branching takes place by means of a 1–6 linkage on mannose units in an irregular manner. The ratio of galactose to mannose in the guar polymer is about one to two.

Locust bean gum is also a polygalactomannan gum of similar molecular structure in which the ratio of galactose to mannose is one to four. Guar and locust bean gum are the preferred sources of the polygalactomannans, principally because of the commercial availability thereof.

In use the polygalactomannan may be either in its natural state (i.e., pure guar gum or locust bean gum) or may be derivatized. Derivatized polygalactomannans include one or more non-ionic and/or ionic groups. Examples of the types of functional groups involved in producing the derivatives include hydroxyalkyl groups, carboxyl group, carboxyalkyl groups, quaternary ammonium groups, sulfonate groups, cyanoalkyl groups, phosphate groups, siloxane groups and the like having varying degrees of substitution and molecular substitution. Specific examples of such polygalactomannans include hydroxypropyl guar, hydroxyethyl guar, carboxymethyl guar, carboxymethyl hydroxypropyl guar, guar hydroxypropyltrimonium chloride and the like having varying degrees of substitution and molar substitution. Such derivatized polygalactomannans are sold by Rhône-Poulenc Inc. under the trade names Jaguar 8000, Jaguar 8710 and Jaguar 8600. Many commercially available starting guar materials may contain small amounts of additives such as borax, glyoxal and the like. These starting materials are expressly intended to constitute part of the present invention.

The term "degree of substitution" as employed herein is the average substitution of functional groups per anhydro sugar unit in the polygalactomannan gums. In guar gum, the basic unit of the polymer consists of two mannose units with a glycosidic linkage and a galactose unit attached to a hydroxyl group of one of the mannose units. On the average, each of the anhydro sugar units contains three available hydroxyl sites. A degree of substitution of three would mean that all of the available hydroxyl sites have been esterified with functional groups. A particularly preferred functional group is the carboxymethyl group, with good results obtained with starting materials having a degree of substitution of between about 0.0 and about 3.0, specifically including materials having a degree of substitution ranging from about 0.05 to about 1.00.

Similarly, the term "molar substitution" as employed herein is the average number of moles of functional groups per anhydro sugar unit in the polygalactomannan gum. A particularly preferred functional group is the hydroxypropyl group, with good results obtained with starting materials having a molar substitution of between about 0.0 and about 3.0. In a preferred embodiment the resulting polysaccharide is carboxymethyl hydroxypropyl guar having a molar substitution of hydroxypropyl groups of between about 0.25 and about 0.35 and a degree of substitution of carboxymethyl groups of between about 0.10 and about 0.15.

Alternative polysaccharide materials which may be selected as the starting material include starches, celluloses and xanthan gum. Examples of starches include both natural and modified starches, such as dextrinated, hydrolyzed, oxidized, cross-linked, alkylated, hydroxyalkylated, acetylated, or fractionated (e.g., amylose and amylopectin). The starch may be of any origin, for example, corn starch, wheat starch, potato starch, tapioca starch, sago starch, rice starch, waxy corn starch or high-amylose corn starch.

Examples of celluloses include hydroxyethyl cellulose, hydroxypropyl cellulose, cellulose gum, carboxymethyl cellulose and alkyl celluloses. Similar to the polygalactomannans, these derivatized materials may have a degree of substitution and/or molar substitution ranging from about 0.0 to about 3.0.

Still other polysaccharides which may be selected as a starting material include polydextrose, chitin/chitosan and derivatives thereof, alginate compositions, carageenan gum, pectin, gum karaya and gum arabic.

Critical to the success of the claimed invention is that the polysaccharide selected have a mean particle size of greater than 200 mesh, as measured by using the Tyler Screen Standard. The applicants have discovered that the use of polysaccharides having such a mean particle size provide an optimal balance between gel strength and absorbency so that the materials are ideal commercial candidates for absorbent compositions. Particularly preferred are the use of polysaccharides having a mean particle size of greater than 100 mesh, with a mean particle size of between about 20 to about 100 mesh being even more preferred.

Such polysaccharides are capable of producing compositions which have excellent gel strength and absorbency properties. With respect to gel strength, the inventive compositions have a gel strength of greater than 2000 dynes/square centimeter, and more preferably compositions have a gel strength of greater than 5000 dynes/square centimeter.

The absorbency properties are defined as the amount of a 0.9% saline solution that can be absorbed by one gram of the inventive material. In practice, the inventive compositions have an absorbency of greater than 15 grams of saline absorbed per gram of composition, with an absorbency of greater than 30 grams of saline absorbed per gram of composition.

The large particle size compositions may be obtained by using any of a number of methods. In one embodiment, the compositions can be prepared by simply agglomerating more fine material such as guar flour so that the final particle size exceeds the minimum 200 mesh. In yet another method, a fine material, such as guar gum flour can be extruded to yield a material having a particle size of greater than 200 mesh.

In still another method, particularly when using polygalactomannans, the use of a coarse grinding technique has demonstrated outstanding results. When using such a method, the first step of the method involves hydrating polygalactomannan splits, preferably guar gum splits by adding water to the splits such that the moisture content of the splits is between about 20 and about 100 percent, more preferably between about 30 and about 80 percent, and most preferably between about 40 and about 60 percent.

While still in a hydrated state, the polygalactomannan splits are then grinded using any grinding technique known in the art. Grinding is accomplished at a level sufficient to produce a composition having a mean particle size in the above described profile. Particularly preferred is grinding to yield particulates having a mean particle size of between about 20 and about 100 mesh.

Thereafter, the ground particulates are dried so that the final moisture content of the composition is less than 20 percent, more preferably less than 15 percent and most preferably less than 10 percent by weight. Drying is accomplished by using means known in the art such as air drying, oven drying, drum drying, filtering, evaporative drying, fluid bed drying, centrifuging, flash grinding, addition of solvents, freeze drying and the like.

In an alternative embodiment, the ground splits may be modified by extruding, flake forming and the like prior to drying. Forms such as flakes, films, sheets, spherical shapes and irregular shapes are all considered to be within the scope of the present invention. The key selection criteria for the final shape of the particulates is primarily dictated by the intended final use for the absorbent material.

As will be shown in the examples, when starting with a fine polysaccharide material having a mean particle size of less than 200 mesh, forming a film of this material followed by coarse grinding does not yield a suitable material as the gel strength and absorbency properties are not sufficient for practical use.

While not necessary to yield efficacious results, it is also possible to crosslink the polysaccharide. Either chemical or physical means may be used to crosslink the polysaccharide. The crosslinking of the inventive materials is considered purely optional.

The agents may be inorganic, organic or organometallic compounds. They may be charge neutral species or ionically charged. Particularly preferred are salts of boron, aluminum, titanium or zirconium. The aluminum, titanium or zirconium metals may form the nonionic, cationic and/or anionic portion of the compound. Other metals which may be selected in accordance with the present invention include hafnium, scandium, yttrium, vanadium, lanthanum, chromium, cerium, zinc, manganese, iron, cobalt, nickel, copper, calcium, magnesium, sodium or potassium or any other metal, including transition metals, which possesses crosslinking properties.

Examples of suitable salts include the acetates, alkoxides such as isopropoxides and hydroxides, halides, lactates, carbonates, nitrates, sulfates and the like. Also useful within the scope of the present invention are the alkali metal and ammonium salts of the respective aluminum, titanium or zirconium cross-linking materials, such as the sodium, potassium or ammonium salts.

Examples of specifically useful cross-linking agents include aluminum acetate, aluminum sulfate, aluminum isopropoxide, aluminum hydroxide, sodium zirconium lactate, zirconium lactate, zirconium acetate, potassium zirconium carbonate, ammoniacal zirconium carbonate, aluminum chloride, titanium acetate and mixtures thereof.

Other crosslinking agents include di, tri and multifunctional organic materials such as dichloroacetic acid, diglycidyl ether and dichlorosuccinic acid. As is the case with the inorganic or organometallic cross-linking agents, the key criteria is not the agent used per se, but rather, the ability of the agent to form a cross-linked polysaccharide which possesses absorbent properties.

Also contemplated within the scope of the present invention is the use of physical means to cross-link the polysaccharide. Such means include the use of heat, vacuum, pressure, surface treatment, mixing and the like.

When crosslinking the compositions of the present invention, a solution or dispersion of the polysaccharide is prepared by adding the polysaccharide to a solvent. Alternatively, the reaction may be performed in a "dry" state where the cross-linking agent is added to a dry polysaccharide and the other optional components. When using a solution reaction, water is the preferred solvent in the polysaccharide solution although other solvents such as alcohols, ethers, glycols, hydrocarbons and mixtures thereof may be used. Addition of the polysaccharide typically takes place at temperatures ranging from about 20° C. to about 90° C., with temperatures between about 40° C. to about 50° C. being most preferred.

The amount of polysaccharide added to the solvent is not critical, the primary consideration being that the polysaccharide be fully wetted (hydrated when the solvent is water). The amount of solvent generally will range from about 1 part to about 200 parts water per part of polysaccharide, preferably from about 30 parts to about 120 parts water per part of polysaccharide. The polysaccharide-solvent solution is allowed to mix for a time sufficient until the polysaccharide is at least substantially completely wetted, preferably completely wetted. To enhance the wetting procedure the mixture may be stirred. Generally from about 5 minutes to about 2 hours will be sufficient for the polysaccharide to be completely wetted. Thereafter, the solution is crosslinked by chemical and/or physical means.

In yet another embodiment, crosslinking may be accomplished by adding a crosslinking agent to the splits. The splits may be hydrated to various levels of hydration and may optionally be derivatized. The crosslinking agent may be added before, during or after derivatization or any combination thereof.

In a preferred embodiment chemical agents, and more preferably aluminum, titanium or zirconium cross-linking agents, including optional auxiliary cross-linking agent are added to the solution in amounts ranging from about 0.01 parts to about 50 parts, more preferably about 0.10 to about 10 parts per 100 parts of polysaccharide. The agent may be added to the solution in neat form, or, more preferably, in a carrier liquid which is preferably the same as the solvent of the solution. This will typically be water. Cross-linking occurs by thoroughly stirring the solution and is demonstrated by the formation of a thixotropic mass. The time required for cross-linking the polysaccharide typically takes between about 5 seconds and about 2 hours, with times ranging from about 1 minute and about 30 minutes being especially preferred. Another preferred embodiment is set forth in Example 4 (i.e., the crosslinking reaction takes place directly on the guar split, which may or may not be derivatized).

Other methods can be used to cross-link the solution such as by adjusting pH, heating and other methods known by those skilled in the art. The rate of cross-linking depends upon such factors as the temperature, pH, amount, rate and degree of mixing, concentration of the cross-linking agent and the like. The cross-linking reaction is completed when the viscosity of the resulting thickened gel-like mass no longer changes or becomes very high. Accordingly, the cross-linked polysaccharide gum may have a consistency ranging from a coherent slowly pourable gel through first stage gelling or gelation in which the thickened mass is no longer pourable but does not have dimensional stability and will spread if unconfined or second stage gelling in which the gel will have some dimensional stability and will temporarily hold a shape but will spread if unconfined for a short period of time.

In practice the novel compositions may be either used alone as absorbents or combined with other chemicals or physical materials to provide potential synergistic absorbency properties. For example, the compositions of the present invention can be combined either prior to or after their synthesis with one or more of the following classes of chemicals: carbohydrates; synthetic hydrophilic polymers; hydroxylated organic compounds; carboxylic acids, their salts and anhydrides; hydroxyacids and their salts; amino acids; proteins and peptides and mixtures thereof. In the case where acid materials are used in combination with the novel polysaccharides of the present invention, their acid salts may alternatively be used.

Specific examples of the above added combined chemicals include sucrose, glucose, lactose, fructose, mannitol, maltose, isomaltulose, gluconic acid, glucoronic acid, glucono-δ-lactone, xylose, sorbose, xylitiol, galactose, mannose, sorbitol, polyvinyl alcohol, polyethylene glycol, polypropylene glycol, polyacrylic acid and its salts, hydrophilic polyacrylates, polyacrylamide, methanol, ethanol, ethylene glycol, propylene glycol, glycerol, formic acid, acetic acid, oxalic acid, succinic acid, maleic acid, fumaric acid, benzoic acid, phthalic acid, 1,2,4,5-benzene tetracarboxylic acid, glycolic acid, lactic acid, citric acid, tartaric acid, aspartic acid, polyaspartic acid, glutamic acid, polyglutamic acid, gelatin, soy protein, beef hydrolysate and mixtures thereof.

Also contemplated for use in association with the present invention is the combination of the novel absorbent composition with commercially viable absorbent compositions. Such materials include crosslinked poyacrylic acid and starch grafted polyacrylic acid. Salts of the above materials may also be combined with the polysaccharide compositions of the present invention.

Also considered for combination with the inventive absorbent polysaccharides of the present invention are the following materials: cellulose fiber, cellulose fluff, peat moss, paper, wood fluffs, cellulose acetate, polyester, polylactide, polyglycolide, polyhydroxybutyrate, polyhydroxyvalerate, polyethylene, polypropylene, polystyrene, polyamide, starch based grafted polymers, cellulose grafted polymers, polyacrylates, polyacetals and mixtures thereof.

In any of the above combinations, the inventive polysaccharides of the present invention should constitute at least 0.01% of the absorbent blend composition.

In addition, for ultimate use as an absorbent material the inventive polysaccharides of the present invention may be combined with one or more of the following additives materials to provide a preferred commercial product: surfactant(s), silicone(s), defoamer(s), silica, diatomaceous earth, alumina, clay and mixtures thereof. Such additives may not function to improve absorbency but rather to complement the absorbent properties of the inventive compositions.

When liquids are added to these inventive compositions and/or blends, the compositions demonstrate an excellent balance of absorbency and gel strength. As such, they are considered good candidates for absorbent materials having a wide variety of use. Generic examples of such uses include diapers, adult incontinence articles, feminine hygiene articles, wound dressings, pet litter, agricultural uses such as hydromulching and soil amendment, automotive filters, underground cables, deodorants, cosmetics, pharmaceuticals, textiles, papers, engineering materials, energy materials, communication material, food materials, waste disposal, sporting goods, gloves such as work gloves, cosmetic gloves, batteries and the like.

Specific uses of the inventive compositions in baby diapers include the following: baby diaper, baby diaper pad, disposable baby diaper, disposable baby diaper pad, flushable baby diaper, flushable baby diaper pad, compostable baby diaper, compostable baby diaper pad, biodegradable baby diaper and biodegradable baby diaper pad.

Specific uses of the inventive compositions in adult diapers include the following: adult diaper, adult diaper pad, disposable adult diaper, disposable adult diaper pad, flushable adult diaper, flushable adult diaper pad, compostable adult diaper, compostable adult diaper pad, biodegradable adult diaper, biodegradable adult diaper pad, adult incontinence pad, adult incontinence diaper, biodegradable adult incontinence diaper and biodegradable adult incontinence pad.

Specific uses of the inventive compositions in feminine hygiene products include the following: feminine napkin, feminine pad, sanitary napkin, disposable feminine napkin, disposable feminine pad, disposable sanitary napkin, compostable feminine napkin, compostable feminine pad, compostable sanitary napkin, flushable feminine napkin, flushable feminine pad, flushable sanitary napkin, biodegradable feminine napkin, biodegradable feminine pad, biodegradable sanitary napkin, tampons, disposable tampons, flushable tampons, compostable tampons, biodegradable tampons, panty shield, panty liner, disposable panty shield, disposable panty liner, compostable panty shield, compostable panty liner, flushable panty shield, flushable panty liner, biodegradable panty shield and biodegradable panty liner.

Specific uses of the inventive compositions in cosmetics products include the following: moisture retention agents, moist towel, towel for make-up application, towel for make-up removal, rheology modifier, thickener, cosmetic emulsifier, hair styling agent, skin conditioner and hair conditioner, fragrance retention agent, fragrance releasing gel, gel deodorant and gel deodorant/antiperspirant.

Specific uses of the inventive compositions in pharmaceutical and medical products include the following: poultice, bandage, wound healing, burn healing, wound dressing, blocking agent for sexually transmitted diseases, burn dressing, blood absorbent, body fluid absorbent, patient bedsheet, absorbing material during and after surgery, transportation and disposal of medical waste, packaging material for the transfer of medical samples, drug delivery system, tablet disintegrant, pharmaceutical formulation and slow release matrix.

Specific uses of the inventive compositions in agriculture and horticulture include the following: water retention agents, plant growth accelerator, coating seedling and plant roots, water retention in flower pots, plant culturing bed, transportation of seedlings and plants, storage of seedlings and plants, growing of seedlings and plants, mushroom farming, fluid sowing, soil improving agent, planting on roads, artificial culture soil, artificial soil for hydroponics, seed coating, seed germination, seeding, slow releasing agent for fertilizer and other agrochemicals, matrix for application of fertilizer and other agrochemicals to prevent runoff, afforestation of desert, hydromulching, transplanting, prevention of soil erosion, interior house plant, food for humans and/or animals, and the like.

Specific uses of the inventive compositions in textile and/or paper products include the following: absorbent sheet, absorbent towel, water absorbent and water proof sheet, dyeing and printing paste and recording material for ink jet recording.

Specific uses of the inventive compositions in construction and/or engineering products include the following: water stop material, sealing materials, slurry shield tunneling, prevention of moisture condensation, desiccant, dehydrating agent, environmental trenching and cement & mortar mixers.

Specific uses of the inventive compositions in energy products include the following: battery paste, water tight electric cable, removal of water from fuel and fuel filter.

Specific uses of the inventive compositions in communication, machinery and instrument products include the following: water tight communication cable, water tight optical fiber cable and joint, desiccant for sensitive instruments and water tight packaging of sensitive instruments.

Specific uses of the inventive compositions in food products include the following: packaging to retain moisture to preserve freshness, water and odor absorbent for food container and drip prevention in trays.

Other miscellaneous uses of the inventive compositions include the following: fire extinguishing, separation of oil and water, dehydrating material, dehydrating waste, dehydrating sludge, transportation and disposal of liquid waste, cold storage agent, chemical pocket heater, cooling agent, dust control, water stop coating material, adhesive, cat litter, toy, controlled release matrix, slow release matrix, media for microbiology, slow release gel for household deodorizing agent, slow release agent for household pesticide and/or insecticide killer, oil field fracturing and/or drilling fluids and fluid loss agent.

In the preferred mode, the above absorbent articles may be designed for throw-away single use applications and they are used in contact with body fluids such as urine, catamenial discharge, perspiration and the like. In its broadest sense, therefore, the present invention provides absorbent articles in which absorbent particles of the cross-linked polysaccharide are contained in, on, or carried by a substrate material, the articles being capable of being held in contact with the body of the user such that the absorbent particles are in contact with body fluids exuded by the body either directly or after passing through a body-contacting cover sheet.

In comparison to the known polyacrylate based materials, the inventive compositions offer advantages because they are more environmentally friendly as they are derived from naturally occurring materials, are biodegradable and less sensitive to salts. Further, as compared to polygalactomannans which have been cross-linked by borate materials as suggested in U.S. Pat. No. 4,333,461 and 4,624,868, and as shown in the Examples to follow, the inventive compositions demonstrate superior performance in terms of absorbency and gel strength.

The invention is described in greater detail by the following non-limiting examples.

EXPERIMENTAL TEST PROCEDURE

The following procedure is used to qualitatively and quantitatively test the properties of the experimental compounds. Saline solution is a 0.9% solution of sodium chloride in distilled water. Sheep blood is citrated.

Absorbency: A nylon bag is prepared using 150 micron (100 mesh) or 20 micron (635 mesh) nylon cloth. The material (approximately 200 mg) is weighed and poured in the bag. The open side of the bag is closed. The bag containing the material is immersed in saline solution (or sheep blood for blood absorbency). After one hour, the bag is taken out from the solution (or sheep blood). The bag is hanged for 30 minutes and weighed to determine the amount of saline solution (or sheep blood) absorbed by the material. The amount of saline solution (or sheep blood) absorbed by one gram of material is defined as the absorbency.

Centrifuge Retention Capacity: The nylon bag containing the saline (or sheep blood) absorbed material from the above experiment is placed over some paper towels inside the basket of a centrifuge (Beckman TJ-6). The centrifuge is operated at 1600 rpm for 3 minutes. The absorbed material in the bag is weighed after centrifugation to determine the amount of saline solution (or sheep blood) retained. The amount of saline solution (or sheep blood) retained by one gram of material is the Centrifuge Retention Capacity (CRC).

Absorbency Under Load: One side of a small cylinder is closed by a stainless steel screen of 100 mesh. Four small pins are attached to the cylinder in such a way that the cylinder could stand on the pins allowing liquid to come through the screen. A small amount (100 mg) of material is evenly distributed on the screen inside the cylinder. The top of the material is covered with a Plexiglas disk and a weight of 100 g is placed on the disk to provide a load of 20 g/cm$^2$ on the material. The cylinder is placed in a container containing the saline solution. After one hour, the cylinder is removed and weighed to determine the amount of saline solution absorbed under the load. The amount of saline solution absorbed under the load by one gram of material is defined as the Absorbency Under Load (AUL).

Gel Strength: The saline solution absorbed material is prepared in the same way as mentioned under absorbency before. The absorbed material is placed between the parallel plates of a Rheometrics Dynamic Spectrometer II. The dynamic shear modulus $G^*$ at 1 $H_z$ is reported as the Gel Strength and expressed in Dynes/cm$^2$

EXAMPLE—1

Distilled water (500 ml) is heated to 180° F. The hot water is added to guar split (weighing 250 g). The mixture is maintained at 180° F. for 15 minutes. The hydrated split has a total moisture content of 63%. The split is grinded in a laboratory blender. The grounded split is dried in a fluid bed drier. The final moisture content is 2.8%. The dried material is separated into various particle sizes by screens of different sieves using the Tyler Screen Standard. The saline absorbency, CRC and gel strength of materials of different particle sizes are determined using a 20 micron (635 mesh) nylon bag and are in Table-1.

TABLE 1

| Particle Size Mesh Size | Absorbency g/g | CRC g/g | Gel Strength Dynes/cm$^2$ |
|---|---|---|---|
| +20* | 18 | 12 | 117900 |
| 20 to 50 | 33 | 19 | 32780 |
| 50 to 100 | 61 | 24 | 8081 |
| 100 to 200 | 10 | 32 | 6494 |
| −200** | 72 | 35 | 1508 |

*particles that will not pass through a 20 mesh screen
**particles that will pass through a 200 mesh screen

EXAMPLE—2

A guar split (3 kg) is hydrated with water (6 l) under nitrogen atmosphere at 180° F. for 15 minutes to a final moisture content of 64.2%. The hydrated split is grinded in a laboratory blender and dried in a fluid bed drier. The dried material is separated into various particle sizes. The absorbency properties are determined using a 150 micron (100 mesh) nylon bag and are tabulated in Table-2.

TABLE 2

| Particle Size Mesh | Saline | | | Sheep Blood | |
|---|---|---|---|---|---|
| | Absorbency g/g | CRC g/g | AUL g/g | Absorbency g/g | CRC g/g |
| +20 | 30 | 18 | 13 | ND | ND |
| 20 to 35 | 32 | 19 | 11 | ND | ND |
| 35 to 50 | 51 | 23 | 9 | 33 | 17 |
| 20 to 50 | 35 | 17 | 10 | ND | ND |
| 50 to 100 | 54 | 24 | 9 | ND | ND |

ND = Not Determined

EXAMPLE—3

The hydrated guar split is passed through a flaker and dried in an oven. The dried product is grinded in a laboratory blender. The materials of different particle sizes were separated. The absorbency properties are determined using 150 micron (100 mesh) nylon bag and are in table-3.

TABLE 3

| Particle Size Mesh | Saline | | | Sheep Blood | |
|---|---|---|---|---|---|
| | Absorbency g/g | CRC g/g | AUL g/g | Absorbency g/g | CRC g/g |
| +20 | 31 | 20 | 10 | ND | ND |
| 20 to 50 | 40 | 21 | 10 | 31 | 15 |
| 50 to 100 | 84 | 28 | 9 | 55 | 21 |

ND = Not Determined

EXAMPLE—4

Guar split (3 kg) is hydrated with water (4 l) at 180° F. for 15 minutes under nitrogen atmosphere. The final moisture content is 55%. To a portion of the hydrated split (2500 g) a solution (28 ml) of sodium zirconium lactate (zirconium content is 5.4%) in water (2 l) is added under nitrogen atmosphere. The product is grinded in a laboratory grinder and dried in a fluid bed drier. The materials of different particle sizes are separated. The absorbency properties are determined using 150 micron (100 mesh) nylon bag and are in table4 below.

TABLE 4

| Particle Size Mesh | Saline | | | Sheep Blood | |
|---|---|---|---|---|---|
| | Absorbency g/g | CRC g/g | AUL g/g | Absorbency g/g | CRC g/g |
| 20 to 50 | 38 | 21 | 11 | 25 | 11 |
| 50 to 100 | 69 | 27 | 9 | 35 | 20 |

EXAMPLE—5

Guar split is converted to carboxymethyl hydroxypropyl guar in the conventional manner by reaction with sodium monochloroacetate and propylene oxide. The carboxymethyl hydroxypropyl guar still in the split form is grinded in a laboratory blender and dried in a fluid bed drier. The dried material is separated into various particle sizes. The absorbency properties are determined using a 150 micron (100 mesh) nylon bag and are tabulated in Table-5.

TABLE 5

| Particle Size Mesh | Saline | | | Sheep Blood | |
|---|---|---|---|---|---|
| | Absorbency g/g | CRC g/g | AUL g/g | Absorbency g/g | CRC g/g |
| +20 | 25 | 15 | 9 | ND | ND |
| 20 to 50 | 54 | 21 | 10 | 32 | 17 |
| 50 to 100 | 82 | 25 | ND | ND | ND |

ND = Not Determined

EXAMPLE—6

The 20 to 50 mesh carboxymethyl hydroxypropyl guar obtained above is heated in an oven at 300° F. for 30 minutes. The saline absorbency properties are determined using a 150 micron (100 mesh) nylon bag. The results are in table-6.

TABLE 6

| Saline | |
|---|---|
| Absorbency: | 50 g/g |
| CRC: | 30 g/g |
| AUL: | 12 g/g |

COMPARATIVE EXAMPLE—7

Commercially available guar powder, (Jaguar 6003-VT from Rhone-Poulenc, 20 g) is added to water (2 l) under rapid mixing. After hydrating at 115° F. in nitrogen atmosphere for 1 hour, the solution is poured in a stainless steel tray. The material is allowed to air dry. The film obtained after drying is grinded in laboratory blender and separated according to particle size. The absorbency properties of the particle size 35 to 50 mesh is determined using 150 micron (100 mesh) nylon bag. The results are in Table-7.

TABLE 7

| Saline | |
|---|---|
| Absorbency: | 11 g/g |
| CRC: | 2 g/g |
| AUL: | 6 g/g |
| Gel Strength: | 308 Dynes/cm$^2$ |
| Sheep Blood | |
| Absorbency: | 20 g/g |
| CRC: | 3 g/g |

EXAMPLE —8

Guar powder (100 g) is taken in a food mixer (Hobart mixer). Water is sprayed over while mixing at a moderate speed. This results in agglomeration of the powder. The mixture is dried in an oven kept at 150° F. for 5 hours. The moisture content of the dried material is 3%.

The product is separated into various particle sizes, their saline absorbency properties are determined and reported in Table-8.

TABLE 8

| Particle Size Mesh | Absorbency g/g | CRC g/g | AUL g/g | Gel Strength Dynes/cm$^2$ |
|---|---|---|---|---|
| 20–50 | 80 | 25 | 9 | 18830 |
| 50–100 | 94 | 30 | 9 | 2456 |

EXAMPLE—9

A dough is made by mixing guar powder (150 g) and water (300 ml). The mixture is placed in a household handheld pasta maker. On compression the long spaghetti type material is obtained. This material is dried in an oven maintained at 120° F. for 16 hours. The dried product has moisture content of 1.5%. The product is grinded in a laboratory grinder and particles of different sizes are separated. The saline absorbency properties are determined and are shown in Table-9.

TABLE 9

| Particle Size Mesh | Absorbency g/g | CRC g/g | AUL g/g | Gel Strength Dynes/cm$^2$ |
|---|---|---|---|---|
| 20–50 | 36 | 15 | 9 | 15430 |
| 50–100 | 75 | 16 | 9 | 256 |

COMPARATIVE EXAMPLE—10

Commercially available guar powder (Jaguar 6003-VT) is separated into particles of various sizes. The relative proportions of various particle sizes are determined. Particles larger than 100 mesh constitutes a negligible fraction (0.5% or less) of the commercial guar powder. The saline absorbency properties of different particle sizes are determined using a 20 micron (635 mesh) bag. The results are in table-10.

TABLE 10

| Particle Size Mesh | Proportion % of total | Absorbency g/g | CRC g/g | Gel Strength Dynes/cm$^2$ |
|---|---|---|---|---|
| 100–200 | 19.5 | 90 | 35 | 232 |
| –200 | 80 | 95 | 35 | 132 |

Having described the invention in detail and by reference to the preferred embodiments thereof, it will be apparent that modifications and variations are possible without departing from the scope of the appended claims.

What is claimed is:

1. An absorbent composition of matter comprising one or more polygalactomannans which, when not in a crosslinked state, has a mean particle size of greater than about 200 mesh, a gel strength of greater than about 2000 dynes per square centimeter and an absorbency of greater than about 15 grams of saline solution per gram of polygalactomannan when immersed in a 0.9% saline solution for a time period of one hour.

2. The composition according to claim 1 further comprising an additional material selected from the group consisting of carbohydrates; natural or synthetic hydrophilic polymers; hydroxylated organic compounds; carboxylic acids; their salts and anhydrides; hydroxyacids and their salts; amino acids; proteins and peptides and mixtures thereof.

3. The composition according to claim 2 wherein said additional material is selected from the group consisting of sucrose, glucose, lactose, fructose, mannitol, maltose, isomaltulose, glucoronic acid and its salts, glucono-δ-lactone, gluconic acid and its salts, xylose, sorbose, xylitiol, galactose, mannose, sorbitol, polyvinyl alcohol, polyethylene glycol, polypropylene glycol, polyacrylic acid and its salts, hydrophilic polyacrylates, polyacrylamide, methanol, ethanol, ethylene glycol, propylene glycol, glycerol, formic acid and its salts, acetic acid and its salts, oxalic acid and its salts, succinic acid and its salts, maleic acid and its salts, fumaric acid and its salts, benzoic acid and its salts, phthalic acid and its salts, 1,2,4,5-benzene tetracarboxylic acid and its salts, glycolic acid and its salts, lactic acid and its salts, citric acid and its salts, tartaric acid and its salts, aspartic acid and its salts, polyaspartic acid and its salts, glutamic acid and its salts, polyglutamic acid and its salts, gelatin, soy protein, beef hydrolysate and mixtures thereof.

4. The composition according to claim 1 further comprising a conventional absorbent material.

5. The composition according to claim 4 wherein said conventional absorbent material is selected from the group consisting of polyacrylic acid and starch grafted polyacrylic acid and mixtures thereof.

6. The composition according to claim 1 further comprising an additive selected from the group consisting of one or more surfactants, one or more defoamers, one or more silicones, silica, diatomaceous earth, alumina, clay and mixtures thereof.

7. The composition according to claim 1 wherein said polygalactomannan comprises guar gum.

8. The composition according to claim 7 wherein said guar gum is derivatized.

9. The composition according to claim 8 wherein said derivatized guar gum is selected from the group consisting of hydroxypropyl guar, hydroxyethyl guar, carboxymethyl guar, carboxymethyl hydroxypropyl guar, guar hydroxypropyltrimonium chloride and mixtures thereof.

10. The composition according to claim 7 which is obtained by either coarse grinding guar gum splits, extruding guar gum flour, forming guar gum flakes or agglomerating guar gum flour.

11. The composition according to claim 7 wherein said guar gum is crosslinked and wherein said guar gum is non-derivatized or derivatized.

12. The composition according to claim 1 which is in the physical form of particles.

13. The composition according to claim 1 which is in the physical form of flakes, films, laminates or sheets.

14. The composition according to claim 1 wherein said polygalactomannan has a mean particle size of greater than about 100 mesh.

15. The composition according to claim 14 wherein said polygalactomannan has a mean particle size of between about 20 mesh and about 100 mesh.

16. The composition according to claim 1 wherein said polygalactomannan has an absorbency of greater than 30 grams of saline solution per gram of composition.

17. The composition according to claim 1 wherein said polygalactomannan has a gel strength of greater than 5000 dynes per square centimeter.

18. An article of manufacture including an absorbent composition of matter comprising one or more polygalactomannans which, when not in a crosslinked state, has a mean particle size of greater than about 200 mesh, a gel strength of greater than about 2000 dynes per square centimeter and an absorbency of greater than about 15 grams of saline solution per gram of polygalactomannan when immersed in a 0.9% saline solution for a time period of one hour.

19. The article according to claim 18 further comprising one or more of the following materials: cellulose fiber, cellulose fluff, peat moss, paper, wood fluffs, cellulose acetate, polyester, polylactide, polyglycolide, polyhydroxybutyrate, polyhydroxyvalerate, polyethylene, polypropylene, polystyrene, polyamide, starch based grafted polymers, cellulose grafted polymers, polyacrylates, polyacetals and mixtures thereof.

20. The article according to claim 18 further comprising an additional material selected from the group consisting of carbohydrates; natural or synthetic hydrophilic polymers; hydroxylated organic compounds; carboxylic acids; their salts and anhydrides; hydroxyacids and their salts; amino acids; proteins and peptides and mixtures thereof.

21. The article according to claim 20 wherein said additional material is selected from the group consisting of sucrose, glucose, lactose, fructose, mannitol, maltose, isomaltulose, gluconic acid and its salts, glucoronic acid and its salts, glucono-δ-lactone, xylose, sorbose, xylitiol, galactose, mannose, sorbitol, polyvinyl alcohol, polyethylene glycol, polypropylene glycol, polyacrylic acid and its salts, hydrophilic polyacrylates, polyacrylamide, methanol, ethanol, ethylene glycol, propylene glycol, glycerol, formic acid and its salts, acetic acid and its salts, oxalic acid and its salts, succinic acid and its salts, maleic acid and its salts, fumaric acid and its salts, benzoic acid and its salts, phthalic acid and its salts, 1,2,4,5-benzene tetracarboxylic acid and its salts, glycolic acid and its salts, lactic acid and its salts, citric acid and its salts, tartaric acid and its salts, aspartic acid and its salts, polyaspartic acid and its salts, glutamic acid and its salts, polyglutamic acid and its salts, gelatin, soy protein, beef hydrolysate and mixtures thereof.

22. The article according to claim 18 further comprising a conventional absorbent material.

23. The article according to claim 20 wherein said conventional absorbent material is selected from the group consisting of polyacrylic acid and starch grafted polyacrylic acid and mixtures thereof.

24. The article according to claim 18 further comprising an additive selected from the group consisting of one or more surfactants, one or more defoamers, one or more silicones, silica, diatomaceous earth, alumina, clay and mixtures thereof.

25. The article according to claim 18 which is selected from the group consisting of baby diapers and diaper pads, adult diapers and pads, feminine hygiene products, cosmetics, deodorants, pharmaceutical materials, medical devices, agricultural products, horticultural products, textile materials, paper materials, construction materials, energy materials, communication materials, food packaging materials, fire extinguishing compositions, separation materials, flocculants, adhesives, pet litter, toys, oil field chemicals, gel materials and microbiological media.

26. The article according to claim 18 wherein said article consists essentially of said absorbent solid composition.

27. The article according to claim 18 wherein said polygalactomannan comprises guar gum.

28. The article according to claim 27 wherein said guar gum is derivatized.

* * * * *